(12) United States Patent
He et al.

(10) Patent No.: US 8,765,196 B2
(45) Date of Patent: Jul. 1, 2014

(54) METHOD FOR SEPARATING AND PURIFYING GINKGOLIDE C FROM ROOT BARK OF GINKGO

(75) Inventors: Jun He, Guizhou (CN); Jichuan Kang, Guizhou (CN); Jianian Yang, Guizhou (CN); Yixin Qian, Guizhou (CN)

(73) Assignee: Guizhou University, Guizhou (CN)

( * ) Notice: Subject to any disclaimer, the term of this patent is extended or adjusted under 35 U.S.C. 154(b) by 0 days.

(21) Appl. No.: 14/006,474

(22) PCT Filed: Feb. 24, 2012

(86) PCT No.: PCT/CN2012/071584
§ 371 (c)(1),
(2), (4) Date: Sep. 20, 2013

(87) PCT Pub. No.: WO2012/126308
PCT Pub. Date: Sep. 27, 2012

(65) Prior Publication Data
US 2014/0039202 A1 Feb. 6, 2014

(30) Foreign Application Priority Data
Mar. 21, 2011 (CN) .......................... 2011 1 0006786

(51) Int. Cl.
*A61K 36/16* (2006.01)
(52) U.S. Cl.
USPC ............................ 424/752; 424/773; 424/775
(58) Field of Classification Search
USPC ........................................................ 424/752
IPC ........................................................ B61K 36/16
See application file for complete search history.

(56) References Cited

U.S. PATENT DOCUMENTS

| | | | | |
|---|---|---|---|---|
| 5,541,183 | A | * | 7/1996 | Park et al. ............ 514/232.8 |
| 6,174,531 | B1 | * | 1/2001 | Zhang et al. ............ 424/752 |
| 6,693,091 | B2 | * | 2/2004 | Stromgaard et al. ........ 514/183 |
| 2003/0031736 | A1 | * | 2/2003 | Lichtblau et al. .......... 424/752 |
| 2003/0152654 | A1 | * | 8/2003 | Xie et al. .................. 424/752 |
| 2003/0225052 | A1 | * | 12/2003 | Stromgaard et al. ........ 514/183 |
| 2008/0108837 | A1 | * | 5/2008 | Nakanishi et al. ........... 549/297 |
| 2009/0156668 | A1 | * | 6/2009 | Vitolo et al. ............... 514/462 |

FOREIGN PATENT DOCUMENTS

| | | | |
|---|---|---|---|
| CN | 1195665 | A | 10/1998 |
| CN | 1847237 | A | 10/2006 |
| CN | 1847237 | A | 10/2006 |
| CN | 101412722 | A | 4/2009 |
| CN | 10174338 | * | 6/2010 |
| CN | 101974014 | A | 2/2011 |
| CN | 102199159 | A | 9/2011 |
| CN | 102464666 | * | 5/2012 |
| CN | 102627656 | * | 8/2012 |

OTHER PUBLICATIONS

PCT/CN2012/071584 International Search Report mailed May 31, 2012, with English translation, 4 pages.
PCT/CN2012/071584 Written Opinion mailed May 31, 2012, with English translation, 11 pages.
PCTCN2012071584 International Search Report mailed May 31, 2012, and English Translation, 4 pages.

* cited by examiner

*Primary Examiner* — Chris R Tate
(74) *Attorney, Agent, or Firm* — Lathrop & Gage LLP

(57) ABSTRACT

Disclosed is a method for separating and purifying Ginkgolide C from root bark of ginkgo. The method comprises: (1) extracting the root bark of ginkgo with ethanol; (2) concentrating the resulting extract under vacuum to remove ethanol; (3) separating the concentrate by macroporous resin column chromatography; (4) after the concentrate being loaded on the column, washing the column with pure water to remove impurities, and then eluting the column with an ethanol solution; (5) concentrating the eluate under vacuum to dryness to obtain a yellow crude extract; (6) heating the crude extract in water to boiling to form a solution, and then refrigerating the solution; (7) concentrating the supernatant solution and filtering under vacuum to obtain a mixed crude crystal of ginkgolides; (8) dissolving the crude crystal in ethanol to form a supersaturated solution, refrigerating and crystallizing the solution to remove Ginkgolides A and B; (9) concentrating and recrystallizing the mother liquor to obtain a crystal of Ginkgolide C; and (10) recrystallizing the crystal with ethanol several times to obtain a high-purity crystal of Ginkgolide C.

9 Claims, No Drawings

METHOD FOR SEPARATING AND PURIFYING GINKGOLIDE C FROM ROOT BARK OF GINKGO

RELATED APPLICATIONS

This application is a national stage entry of PCT Application No. PCT/CN2012/071584, filed Feb. 24, 2012, which claims priority to Chinese Application No. 201110067186.9, filed Mar. 21, 2011. Each of the aforementioned applications are incorporated by reference herein.

FIELD OF THE INVENTION

The invention relates to a ginkgolide, and specifically to a method for separating and purifying Ginkgolide C in high purity from the root bark of ginkgo.

BACKGROUND OF THE INVENTION

Ginkgolide compounds belong to terpenoids and are also known as ginkgo terpene lactones which are composed of sesquiterpene lactones and diterpene lactones. Moreover, they are an important active ingredient in leaves of ginkgo.

Ginkgolide C is a diterpene lactone compound, which was firstly separated from leaves of ginkgo by S. Furukawa in 1932, and was further separated and identified the chemical structure thereof by K. Nakanish, M. Maruyama and K. Okabe, et al. in 1967. Ginkgolide compounds have a molecular skeleton consisting of 20 carbon atoms and having 6 five-membered rings: 2 five-membered carbocyclic rings, 3 five-membered lactone rings, and 1 tetrahydrofuran ring, in which 2 five-membered carbocyclic rings are linked together in the form of a spiro ring, and the other rings are fused together, so as to form the following particular rigid cage stereochemical structure.

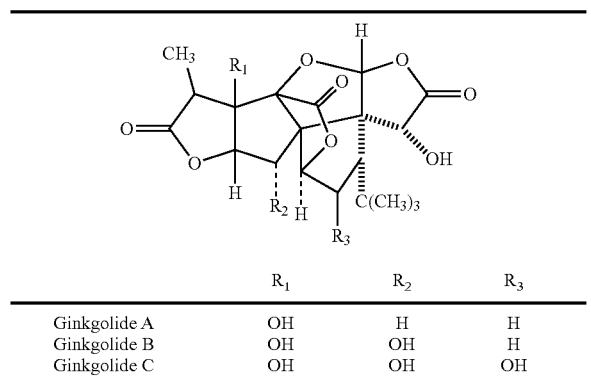

| | $R_1$ | $R_2$ | $R_3$ |
|---|---|---|---|
| Ginkgolide A | OH | H | H |
| Ginkgolide B | OH | OH | H |
| Ginkgolide C | OH | OH | OH |

All the ginkgolides have a potent antagonist of platelet activating factor, and are a particular active ingredient in each part of ginkgo plant. The content of the ginkgolides is highest in the root bark of ginkgo, which is about three times of that in ginkgo leaves. The ginkgolide compounds are bitter white crystals with the melting point of about 300° C. Because a hydroxy group/hydroxy groups and several oxygen-containing ester groups are present in molecule, the ginkgolide compounds have higher polarity than common sesquiterpene and diterpene compounds, and are soluble in organic solvents such as ethanol, acetone, butanone, ethyl acetate, dimethyl sulfoxide and the like.

The ginkgolide compounds are very stable against concentrated acids and strong oxidants. After a ginkgolide compound is dissolved in concentrated nitric acid and then evaporated to dryness, the lactone thereof would not be destroyed. The ginkgolide compound comprises several lactone structures in molecule. The ginkgolide compound can be reacted with a base to produce a salt which is soluble in water. If the resulting salt is acidified with an acid, it will convert to the initial lactone which is insoluble in water but soluble in an organic solvent. Therefore, this property can be used for the extraction and separation of ginkgolides.

Currently, many studies are focused on the separation and purification of the ginkgolides from leaves of ginkgo, but there are few reports regarding the separation and purification of ginkgolides from root bark of ginkgo. The ginkgolides from leaves of ginkgo are generally obtained by extracted, separated on columns, and then further separated by a high performance liquid preparative chromatography to achieve a purity of 95%. That is, macroporous adsorptive resin only contributes to the removal of impurities and the enrichment in the process, but does not actually contribute to the purification. Moreover, the use of $C_{18}$ column increases the process steps and production cost, so that the entire process for separation and purification is relatively complex, the yield is low, the cost is expensive, and a mass production is difficult to carry out. Only one patent application with application No. 201010294667.9, titled "A PROCESS FOR EXTRACTING GINKOGLIDES A AND C FROM ROOT BARK OF GINKGO", relates to the separation and purification of ginkgolides from the root bark of ginkgo. However, the technical solution of the patent application can only obtain a mixture of Ginkgolides A and C, and cannot directly offer a high-purity Ginkgolide C.

DISCLOSURE OF THE INVENTION

An object of the invention is to provide a method for separating and purifying Ginkgolide C from the root bark of ginkgo, which is a simple and convenient method for separating and purifying Ginkgolide C and suitable for industrial production. The method can overcome the drawbacks in the prior art, such as the complex process flow, the low yield, the poor selectivity of separation and purification, and the high cost of industrial production as well as the final product not suitable for direct use as a pharmaceutical raw material.

The inventor provides a method carried out by the following steps:

(1) extracting the root bark of ginkgo as a raw material with 50% by weight of ethanol;

(2) concentrating the resulting extract under vacuum to remove ethanol;

(3) separating the concentrate by macroporous resin column chromatography;

(4) after the concentrate being loaded on the column, washing the column with 2 folds column volume of pure water to remove impurities, and then eluting the column with 80% to 95% by weight of an ethanol solution;

(5) concentrating the eluate under vacuum to dryness to obtain a yellow crude extract;

(6) heating the crude extract in water to boiling to form a solution, and then refrigerating the solution;

(7) concentrating the supernatant solution to ⅕ volume of the initial volume to produce a large number of lactone particles, and then filtering under vacuum with filter paper to obtain a white mixed crude crystal of ginkgolides;

(8) dissolving the crude crystal in 95% by weight of ethanol to form a supersaturated solution, refrigerating and crystallizing the solution to remove Ginkgolides A and B;

(9) concentrating and recrystallizing the mother liquor to obtain a crystal of Ginkgolide C with a content of more than 80%; and

(10) recrystallizing the crystal with ethanol several times to obtain a high-purity crystal of Ginkgolide C.

In the step (1), 50% by weight of ethanol is added at a material-liquid ratio of 1:8, and the resulting mixture is heated to 70° C. to extract for 2 hours.

In the step (2), the extract is concentrated under a vacuum degree of 0.08 MPa and a temperature of 60° C. to 70° C. until no taste of ethanol is present. At this moment, the volume of the concentrate is about ⅓ of the initial extract volume.

In the step (3), the type of the resin used in the column chromatography is DM130, D101 or AB-8.

In the step (4), the pure water for removing impurities is neutral, and the amount of the pure water is 2 folds column volume; the amount of 80% to 90% by weight of ethanol for eluting is 3-4 folds column volume.

In the step (5), the eluate is concentrated under a vacuum degree of 0.08 MPa and a temperature of 60° C. to 70° C.

In the step (6), the solution is refrigerated at a temperature of 2° C. to 6° C. for 12 hours.

In the step (7), the supernatant solution is concentrated under a vacuum degree of 0.08 MPa and a temperature of 60° C.

In the step (10), the crystal is recrystallized three times.

The inventor points out that: during the extraction process of step (1), the use of 50% by weight of ethanol for extraction is preferable to water because of the following reasons: first of all, the use of 50% by weight of ethanol for extraction results in a higher extraction ratio of lactones than water; secondly, the extract of water contains more proteins and polysaccharide substances which is not suitable for being loaded on column, while the use of the aqueous alcohol solution can reduce the proteins and polysaccharide substances in the extract to reduce the viscosity of the solution, which is suitable for being loaded on column.

The inventor further points out that: in the step (8), the crude crystal is dissolved in 95% by weight of ethanol to form a supersaturated solution, and then undergoes fractional crystallization according to the polarity of the lactones to remove Ginkgolide A and Ginkgolide B, namely, Ginkgolide B is firstly crystallized out and the mother liquor is suitably concentrated to crystallize Ginkgolide A, thus the mother liquor mainly comprises Ginkgolide C and little Ginkgolide A; the mother liquor is further concentrated to obtain a crystal of Ginkgolide C with the content of more than 80%, in which less than 5% of Ginkgolide A is present.

The method of the invention can obtain a high-purity Ginkgolide C with a purity of more than 97% by the separation and purification from the root bark of ginkgo. Moreover, the method of the invention has advantages such as the simple process flow, the good product quality and the low cost of industrial production and so on.

SPECIFIC MODE FOR CARRYING OUT THE INVENTION

The invention will be further illustrated by the following examples.

EXAMPLE 1

(1) 800 L of 50% ethanol was added to 100 kg of root bark of ginkgo, and the resulting mixture was heated to 70° C. to extract for 2 hours;

(2) the extract was concentrated under vacuum to remove ethanol, and the concentration was conducted under a vacuum degree of 0.08 MPa and a temperature of 60° C. to 70° C. until no taste of ethanol was present, and the volume of the concentrate was about 200 L;

(3) the concentrate was separated by macroporous resin column chromatography, the type of the resin was AB-8, the amount of the resin was 100 kg, and the diameter-height ratio of the column was 1:8 or 1:10;

(4) after the concentrate was loaded on the column, the column was washed with 200 L of pure water to remove impurities, and then was eluted with 300 L to 400 L of 80% to 95% by weight of an ethanol solution;

(5) the eluate was concentrated under vacuum, and the concentration was conducted under a vacuum degree of 0.08 MPa and a temperature of 60° C. to 70° C., so as to obtain a reddish brown extractum;

(6) the reddish brown extractum was heated in water to boiling to form a solution, and then the solution was refrigerated at 2° C. to 6° C. over night;

(7) the supernatant solution was concentrated to ⅕ volume of the initial volume to produce a large number of lactone particles, and then filtered under vacuum with filter paper to obtain a white mixed crude crystal of Ginkgolides A, B and C;

(8) the crude crystal was dissolved in 95% by weight of ethanol to form a supersaturated solution, and then underwent fractional crystallization to remove Ginkgolides A and B;

(9) the mother liquor was further concentrated until a large number of crystals emerged, and then filtered under vacuum to obtain a crystal of Ginkgolide C with a content of more than 80%;

(10) the crystal was dissolved in 95% ethanol and recrystallized several times to obtain 110 g of a high-purity crystal of Ginkgolide C.

EXAMPLE 2

(1) 500 L of water was added to 50 kg of root bark of ginkgo, and the resulting mixture was extracted under the condition same as that of Example 1;

(2) the filtrate was loaded on macroporous resin column, and then separated via dynamic adsorption by D101 resin;

(3)-(9) were same as those of Example 1 to obtain 50 g of a crystal of Ginkgolide C with a purity of more than 97%.

What is claimed is:

1. A method for separating and purifying Ginkgolide C from root bark of ginkgo, comprising the steps of:
(1) extracting the root bark of ginkgo as a raw material with 50% by weight of ethanol;
(2) concentrating the resulting extract under vacuum to remove ethanol;
(3) loading the resulting concentrate on a macroporous resin column chromatography;
(4) washing the column with 2 folds column volume of pure water to remove impurities, and then eluting the column with 80% to 95% by weight of an ethanol solution;
(5) concentrating the eluate under vacuum to dryness to obtain a yellow crude extract;
(6) heating the crude extract in water to boiling to form a solution, and then refrigerating the solution;
(7) obtaining a supernatant from the refrigerated solution and concentrating the supernatant to ⅕ volume of the initial volume to produce a large number of lactone particles, and then filtering under vacuum with filter paper to obtain a white mixed crude crystal of ginkgolides;

(8) dissolving the crude crystal in 95% by weight of ethanol to form a supersaturated solution, refrigerating and crystallizing the supersaturated solution to remove Ginkgolides A and B;

(9) concentrating and recrystallizing the resulting solution to obtain a crystal of Ginkgolide C with a content of more than 80%; and

(10) recrystallizing the crystal with ethanol several times to obtain a high-purity crystal of Ginkgolide C.

2. The method according to claim 1, wherein in the step (1), 50% by weight of ethanol is added at a material-liquid ratio of 1:8, and the resulting mixture is heated to 70° C. to extract for 2 hours.

3. The method according to claim 1, wherein in step (2), the extract is concentrated under a vacuum degree of 0.08 MPa and a temperature of 60° C. to 70° C. until no taste of ethanol is present.

4. The method according to claim 1, wherein in step (3), the type of the resin is DM130, D101 or AB-8.

5. The method according to claim 1, wherein in step (4), the pure water for removing the impurities is neutral, the amount of the pure water is 2 folds column volume; and the amount of 80% to 95% by weight of ethanol for eluting is 3-4 folds column volume.

6. The method according to claim 1, wherein in step (5), the eluate is concentrated under a vacuum degree of 0.08 MPa and a temperature of 60° C. to 70° C.

7. The method according to claim 1, wherein in the step (6), the solution is refrigerated at a temperature of 2° C. to 6° C. for 12 hours.

8. The method according to claim 1, wherein in the step (7), the supernatant is concentrated under a vacuum degree of 0.08 MPa and a temperature of 60° C.

9. The method according to claim 1, wherein in the step (10), the crystal is recrystallized three times.

* * * * *